(12) United States Patent
Kawamura

(10) Patent No.: US 10,916,011 B2
(45) Date of Patent: Feb. 9, 2021

(54) BONE MINERAL INFORMATION ACQUISITION APPARATUS, BONE MINERAL INFORMATION ACQUISITION METHOD, AND BONE MINERAL INFORMATION ACQUISITION PROGRAM

(71) Applicant: FUJIFILM CORPORATION, Tokyo (JP)

(72) Inventor: Takahiro Kawamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 69 days.

(21) Appl. No.: 16/382,160

(22) Filed: Apr. 11, 2019

(65) Prior Publication Data

US 2019/0362492 A1    Nov. 28, 2019

(30) Foreign Application Priority Data

May 25, 2018  (JP) ................................. 2018-100422

(51) Int. Cl.
*G06T 7/00*       (2017.01)
*A61B 6/00*       (2006.01)

(52) U.S. Cl.
CPC ............ *G06T 7/0012* (2013.01); *A61B 6/505* (2013.01)

(58) Field of Classification Search
CPC combination set(s) only.
See application file for complete search history.

(56) References Cited

U.S. PATENT DOCUMENTS

| 2005/0010106 A1* | 1/2005 | Lang ...................... A61B 6/469 600/425 |
| 2007/0047794 A1* | 3/2007 | Lang ..................... G06T 7/0012 382/132 |
| 2008/0031412 A1* | 2/2008 | Lang .................... G01B 15/045 378/54 |
| 2011/0036360 A1* | 2/2011 | Lang ........................ G06T 7/20 128/898 |
| 2011/0040168 A1* | 2/2011 | Arnaud ................. G06T 7/0012 600/407 |
| 2011/0064193 A1* | 3/2011 | Minnigh ................ A61B 6/505 378/62 |

(Continued)

FOREIGN PATENT DOCUMENTS

JP       2018-15453 A      2/2018

*Primary Examiner* — Omar S Ismail
(74) *Attorney, Agent, or Firm* — Solaris Intellectual Property Group, PLLC

(57) ABSTRACT

A body thickness estimation unit estimates a body thickness of a subject for each pixel of at least one of a first radiographic image or a second radiographic image which includes a primary ray component and a scattered ray component, on the basis of the at least one of the first radiographic image or the second radiographic image. A bone part pixel value acquisition unit acquires a pixel value of a bone region of the subject from the first and second radiographic images. An information acquisition unit acquires bone mineral information indicating a bone mineral content of the bone region for each pixel of the bone region on the basis of imaging conditions in a case in which the at least one of the first radiographic image or the second radiographic image has been acquired, the body thickness for each pixel, and the pixel value of the bone region.

20 Claims, 13 Drawing Sheets

(56) References Cited

U.S. PATENT DOCUMENTS

| | | | |
|---|---|---|---|
| 2012/0059239 A1* | 3/2012 | Yamaguchi | A61B 6/463 600/407 |
| 2013/0315372 A1* | 11/2013 | Behiels | A61B 6/4216 378/62 |
| 2013/0343519 A1* | 12/2013 | Ma | A61B 6/542 378/54 |
| 2013/0343521 A1* | 12/2013 | Lee | A61B 6/5241 378/62 |
| 2016/0015347 A1* | 1/2016 | Bregman-Amitai | A61B 6/481 382/131 |
| 2016/0220213 A1* | 8/2016 | Miyamoto | A61B 6/5258 |
| 2017/0273652 A1* | 9/2017 | Tajima | A61B 6/461 |
| 2018/0008224 A1* | 1/2018 | Arima | G06T 7/0012 |

* cited by examiner

AMOUNT OF
BONE MINERAL

LARGE

SMALL

BONE STRENGTH

HIGH

LOW

AMOUNT OF
BONE MINERAL
LARGE
↕
SMALL

AMOUNT OF
BONE MINERAL

LARGE

SMALL

AMOUNT OF
BONE MINERAL

LARGE

SMALL

BONE MINERAL INFORMATION ACQUISITION APPARATUS, BONE MINERAL INFORMATION ACQUISITION METHOD, AND BONE MINERAL INFORMATION ACQUISITION PROGRAM

CROSS REFERENCE TO RELATED APPLICATIONS

The present application claims priority under 35 U.S.C. § 119 to Japanese Patent Application No. 2018-100422 filed on May 25, 2018. The above application is hereby expressly incorporated by reference, in its entirety, into the present application.

BACKGROUND

Technical Field

The present disclosure relates to a bone mineral information acquisition apparatus, a bone mineral information acquisition method, and a bone mineral information acquisition program that acquire bone mineral information using a radiographic image including a bone.

Related Art

Dual X-ray absorptiometry (DXA) has been known as a representative bone mineral quantitation method used to diagnose bone density in a bone disease such as osteoporosis. The DXA method calculates bone mineral content from the pixel values of radiographic images obtained by imaging with radiations having two types of energy levels, using the fact that radiation which is incident on the human body and is transmitted through the human body is attenuated by a mass attenuation coefficient $\mu$ ($cm^2/g$) depending on a substance (for example, bone) forming the human body, the density $\rho$ ($g/cm^3$) of the substance, and the thickness t (cm) of the substance.

In addition, a radiography apparatus has been known which comprises two radiation detectors that include a plurality of pixels accumulating charge corresponding to emitted radiation and are provided so as to be stacked. Further, a technique has been known which measures the bone mineral content of a subject using each electric signal corresponding to the amount of radiation emitted to each radiation detector in this type of radiography apparatus (see JP2018-015453A).

However, in a case in which radiographic images are acquired, scattered rays are generated due to the scattering of radiation in the subject. In the DXA method, the subject is irradiated with radiation such that the influence of scattered rays is reduced. In order to acquire bone mineral information using the DXA method, a dedicated apparatus for irradiating the subject with radiation is required as described above. Therefore, it is difficult to use the existing facilities. In addition, since the DXA method calculates bone mineral content for each bone, it is difficult to evaluate bone mineral information for each part of the bone.

SUMMARY

The present disclosure has been made in view of the above-mentioned problems and an object of the present disclosure is to provide a technique that can acquire bone mineral information using the existing facilities.

According to an aspect of the present disclosure, there is provided a bone mineral information acquisition apparatus comprising: a body thickness estimation unit that estimates a body thickness of a subject including a bone part and a soft part for each pixel of at least one of a first radiographic image or a second radiographic image which includes a primary ray component and a scattered ray component on the basis of the at least one of the first radiographic image or the second radiographic image, the first and second radiographic images being acquired by radiations that have different energy distributions and have been transmitted through the subject; a bone part pixel value acquisition unit that acquires a pixel value of a bone region of the subject from the first and second radiographic images; and an information acquisition unit that acquires bone mineral information indicating a bone mineral content of the bone region for each pixel of the bone region on the basis of imaging conditions in a case in which the at least one image has been acquired, the body thickness for each pixel, and the pixel value of the bone region.

In the bone mineral information acquisition apparatus according to the aspect of the present disclosure, the first and second radiographic images may be acquired by irradiating two detectors that overlap each other with the radiation transmitted through the subject.

In the bone mineral information acquisition apparatus according to the aspect of the present disclosure, the first and second radiographic images may be acquired by alternately irradiating one detector with the radiations that have different energy distributions and have been transmitted through the subject.

In the bone mineral information acquisition apparatus according to the aspect of the present disclosure, the information acquisition unit may acquire the bone mineral information by converting the pixel value of the bone region into a pixel value of the bone region acquired on the basis of a reference imaging condition.

In the bone mineral information acquisition apparatus according to the aspect of the present disclosure, the reference imaging condition may be a tube voltage that is applied to a radiation source in a case in which the first and second radiographic images are acquired.

In the bone mineral information acquisition apparatus according to the aspect of the present disclosure, the information acquisition unit may acquire the bone mineral information by converting the pixel value of the bone region on the basis of a correction coefficient corresponding to at least one of information on the reference imaging condition, information on beam hardening corresponding to the body thickness, or information on whether a scattered ray removal grid is present during imaging.

The bone mineral information acquisition apparatus according to the aspect of the present disclosure may further comprise a display controller that displays information related to the bone mineral information on a display unit.

The information related to the bone mineral information includes new information calculated from the bone mineral information and new information calculated from information other than the bone mineral information. In addition, the related information may be the bone mineral information.

In the bone mineral information acquisition apparatus according to the aspect of the present disclosure, the display controller may display, as the related information, a soft part image indicating a soft region of the subject, a bone part image indicating the bone region of the subject, and a composite image obtained by superimposing the bone mineral information on the first radiographic image or the second radiographic image on the display unit, the soft part image and the bone part image being acquired from the first and second radiographic images.

In the bone mineral information acquisition apparatus according to the aspect of the present disclosure, the display controller may display bone strength calculated from the bone mineral information as the related information on the display unit.

In the bone mineral information acquisition apparatus according to the aspect of the present disclosure, in a case in which the subject includes a plurality of bones, the display controller may display the related information acquired for each bone on the display unit.

In the bone mineral information acquisition apparatus according to the aspect of the present disclosure, the display controller may display the related information on a partial region in the bone region on the display unit.

In the bone mineral information acquisition apparatus according to the aspect of the present disclosure, the partial region may be a cancellous bone region in the bone region.

In the bone mineral information acquisition apparatus according to the aspect of the present disclosure, in a case in which the subject includes a plurality of bones, the display controller may display a comparison result between the bone mineral information items of the bones as the related information on the display unit.

In the bone mineral information acquisition apparatus according to the aspect of the present disclosure, the display controller may display a comparison result between the bone mineral information items of the partial regions in the bone region as the related information on the display unit.

In the bone mineral information acquisition apparatus according to the aspect of the present disclosure, the display controller may display a comparison result between the bone mineral information and past bone mineral information acquired at different dates and times for the same subject as the related information on the display unit.

In the bone mineral information acquisition apparatus according to the aspect of the present disclosure, in a case in which the bone region is a vertebra region, the display controller may display, as the related information, information indicating a bone fracture risk which is generated from spinal alignment and the bone mineral information on the display unit.

The bone mineral information acquisition apparatus according to the aspect of the present disclosure may further comprise a related information generation unit that generates the related information.

According to another aspect of the present disclosure, there is provided a bone mineral information acquisition method comprising: estimating a body thickness of a subject including a bone part and a soft part for each pixel of at least one of a first radiographic image or a second radiographic image which includes a primary ray component and a scattered ray component, on the basis of the at least one of the first radiographic image or the second radiographic image, the first and second radiographic images being acquired by radiations that have different energy distributions and have been transmitted through the subject; acquiring a pixel value of a bone region of the subject from the first and second radiographic images; and acquiring bone mineral information indicating a bone mineral content of the bone region for each pixel of the bone region on the basis of imaging conditions in a case in which the at least one image has been acquired, the body thickness for each pixel, and the pixel value of the bone region.

A program that causes a computer to perform the bone mineral information acquisition method according to the aspect of the present disclosure may be provided.

A bone mineral information acquisition apparatus according to another aspect of the present disclosure comprises a memory that stores commands to be executed by a computer and a processor configured to execute the stored commands. The processor performs: a process of estimating a body thickness of a subject including a bone part and a soft part for each pixel of at least one of a first radiographic image or a second radiographic image which includes a primary ray component and a scattered ray component on the basis of the at least one of the first radiographic image or the second radiographic image, the first and second radiographic images being acquired by radiations that have different energy distributions and have been transmitted through the subject; a process of acquiring a pixel value of a bone region of the subject from the first and second radiographic images; and a process of acquiring bone mineral information indicating a bone mineral content of the bone region for each pixel of the bone region on the basis of imaging conditions in a case in which the at least one image has been acquired, the body thickness for each pixel, and the pixel value of the bone region.

According to the present disclosure, the body thickness of the subject is estimated for each pixel of at least one of the first radiographic image or the second radiographic image and the pixel value of the bone region of the subject is acquired from the first and second radiographic images. Then, bone mineral information indicating the bone mineral content of the bone region is acquired for each pixel of the bone region on the basis of the imaging conditions in a case in which the at least one of the first radiographic image or the second radiographic image has been acquired, the body thickness for each pixel, and the pixel value of the bone region. Therefore, it is possible to acquire the bone mineral information without using a dedicated apparatus unlike the DXA method. In addition, since the bone mineral information is acquired for each pixel of the bone region, it is possible to evaluate the bone mineral information for each part of the bone.

DETAILED DESCRIPTION

Figure 1:
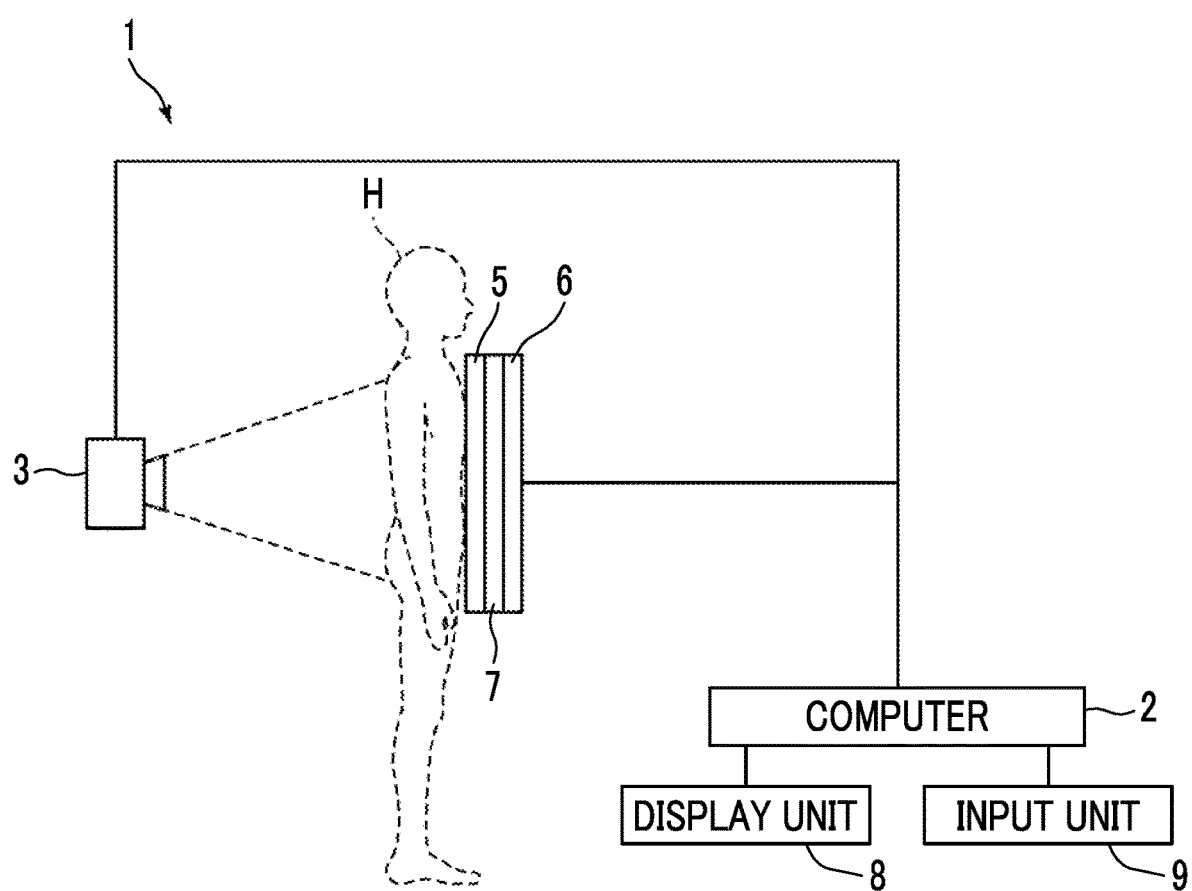
FIG. 1 is a block diagram schematically illustrating the configuration of a radiography system to which a bone mineral information acquisition apparatus according to an embodiment of the present disclosure is applied.

Hereinafter, an embodiment of the present disclosure will be described with reference to the drawings. FIG. 1 is a block diagram schematically illustrating the configuration of a radiography system to which a bone mineral information acquisition apparatus according to the embodiment of the present disclosure is applied. As illustrated in FIG. 1, the radiography system according to this embodiment captures two radiographic images with different energy distributions and acquires bone mineral information using the two radiographic images. The radiography system comprises an imaging apparatus 1 and a computer 2 including the bone mineral information acquisition apparatus according to this embodiment.

The imaging apparatus 1 performs so-called one-shot energy subtraction that irradiates a first radiation detector 5 and a second radiation detector 6 with X-rays which have been emitted from an X-ray source 3 as a radiation source and then transmitted through a subject H while changing energy. In a case in which imaging is performed, as illustrated in FIG. 1, the first radiation detector 5, an X-ray energy conversion filter 7 which is, for example, a copper plate, and the second radiation detector 6 are arranged in this order from the X-ray source 3 and the X-ray source 3 is driven. In addition, the first and second radiation detectors 5 and 6 and the X-ray energy conversion filter 7 come into close contact with each other.

With this configuration, the first radiation detector 5 acquires a first radiographic image G1 of the subject H obtained by low-energy X-rays including so-called soft rays. In addition, the second radiation detector 6 acquires a second radiographic image G2 of the subject H obtained by high-energy X-rays without soft rays. The first and second radiographic images are input to the computer 2 which is the bone mineral information acquisition apparatus. In this embodiment, in a case in which an image of the subject H is captured, a scattered ray removal grid that removes scattered ray components of the X-rays transmitted through the subject H is not used. Therefore, the first radiographic image G1 and the second radiographic image G1 include primary ray components and scattered ray components of the X-rays transmitted through the subject H.

The first and second radiation detectors 5 and 6 can repeatedly perform the recording and reading of radiographic images and may be a so-called direct-type radiation detector that is directly irradiated with radiation and generates charge or a so-called indirect-type radiation detector that converts radiation into visible light and then converts the visible light into a charge signal. In addition, it is preferable to use a so-called TFT reading method that turns on and off a thin film transistor (TFT) switch to read a radiographic image signal or a so-called light reading method that emits reading light to read a radiographic image signal as a radiographic image signal reading method.

A display unit 8 and an input unit 9 are connected to the computer 2. The display unit 8 is, for example, a cathode ray tube (CRT) or a liquid crystal display and assists the input of radiographic images acquired by imaging and various types of data required for processes performed in the computer 2. The input unit 9 is, for example, a keyboard, a mouse, or a touch panel.

A bone mineral information acquisition program according to this embodiment is installed in the computer 2. In this embodiment, the computer may be a workstation or a personal computer that is directly operated by an operator or may be a server computer that is connected to the workstation or the personal computer through a network. The bone mineral information acquisition program is recorded on a recording medium, such as a digital versatile disc (DVD) or a compact disc read only memory (CD-ROM), is distributed, and is installed in the computer from the recording medium. Alternatively, the bone mineral information acquisition program is stored in a storage device of a server computer connected to the network or a network storage so as to be accessed from the outside and is downloaded and installed in the computer if necessary.

Figure 2:
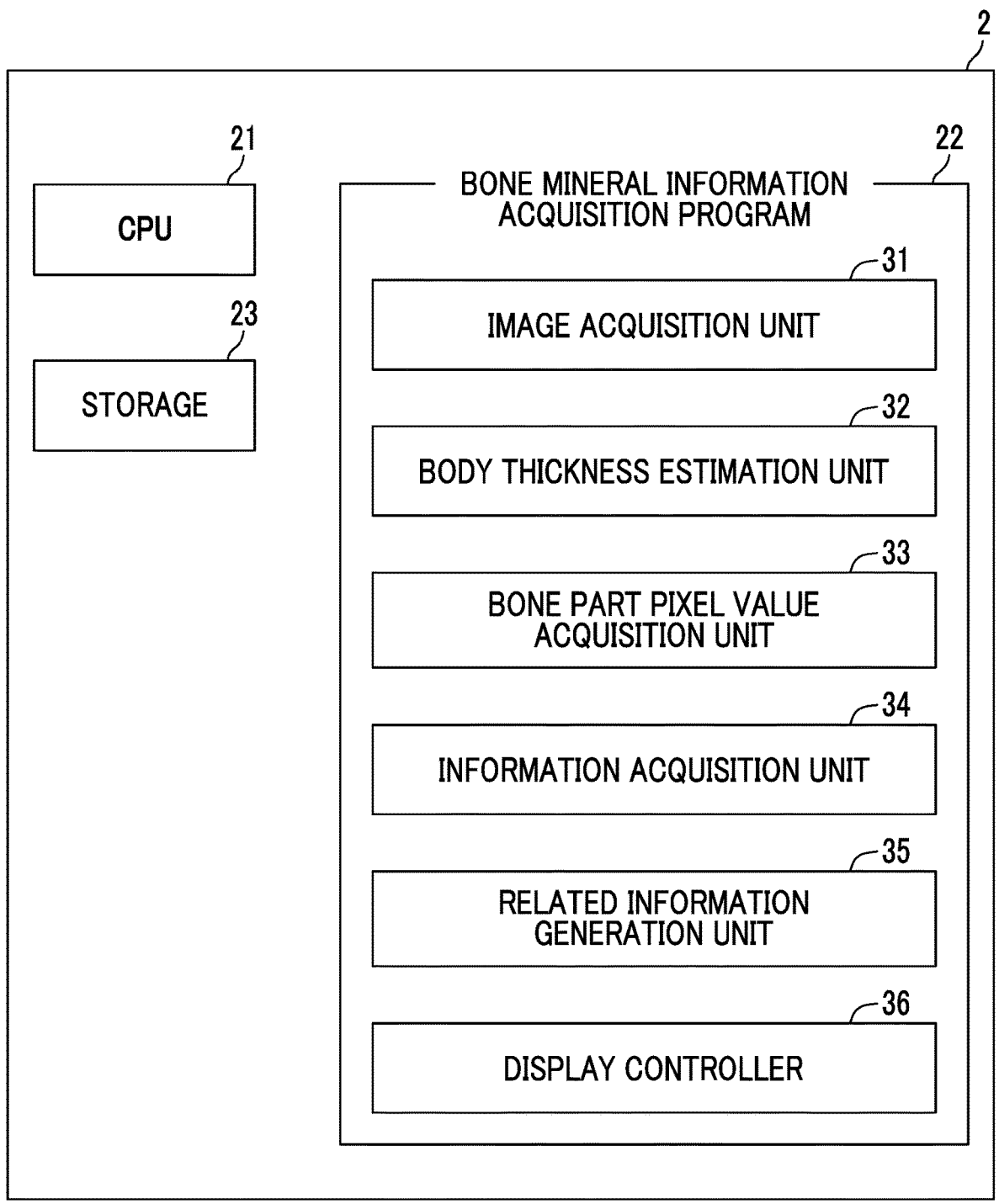
FIG. 2 is a diagram schematically illustrating the configuration of the bone mineral information acquisition apparatus according to this embodiment.

FIG. 2 is a diagram schematically illustrating the configuration of the bone mineral information acquisition apparatus implemented by installing the bone mineral information acquisition program in the computer 2 in this embodiment. As illustrated in FIG. 2, the bone mineral information acquisition apparatus comprises a central processing unit (CPU) 21, a memory 22, and a storage 23 as the configuration of a standard computer.

The storage 23 is a storage device, such as a hard disk drive or a solid state drive (SSD), and stores various kinds of information including programs for driving each unit of the imaging apparatus 1 and the bone mineral information acquisition program. In addition, the storage 23 stores radiographic images acquired by imaging.

For example, the programs stored in the storage 23 are temporarily stored in the memory 22 in order to cause the CPU 21 to perform various processes. The bone mineral information acquisition program defines, as processes performed by the CPU 21, an image acquisition process of causing the imaging apparatus 1 to perform imaging to acquire the first and second radiographic images G1 and G2 which have different energy distributions and each of which includes primary ray components and scattered ray components, a body thickness estimation process of estimating the body thickness of the subject H for each pixel of at least one of the first radiographic image G1 or the second radiographic image G2 on the basis of at least one of the first radiographic image G1 or the second radiographic image G2, a bone part pixel value acquisition process of acquiring a pixel value of a bone region of the subject H from the first and second radiographic images G1 and G2, an information acquisition process of acquiring bone mineral information indicating the bone mineral content of the bone region for each pixel of the bone region on the basis of imaging conditions in a case in which at least one of the first radiographic image G1 or the second radiographic image G2 has been acquired, the body thickness for each pixel, and the pixel value of the bone region, a related information generation process of generating information related to the bone mineral information, and a display control process of displaying the related information on the display unit.

Then, the CPU 21 performs these processes according to the bone mineral information acquisition program to make the computer 2 function as an image acquisition unit 31, a body thickness estimation unit 32, a bone part pixel value acquisition unit 33, an information acquisition unit 34, a related information generation unit 35, and a display controller 36. In addition, in this embodiment, the CPU 21 executes the bone mineral information acquisition program to function as each unit. However, in addition to the CPU 21, a programmable logic device (PLD) that is a processor whose circuit configuration can be changed after manufacture, such as a field programmable gate array (FPGA), can be used as a general-purpose processor that executes software to function as various processing units. Further, the process of each unit may be performed by a dedicated electric circuit, such as an application specific integrated circuit (ASIC), which is a processor having a dedicated circuit configuration designed to perform a specific process.

One processing unit may be configured one of the various processors or a combination of two or more processors of the same type or different types (for example, a combination of a plurality of FPGAs and a combination of a CPU and an FPGA). In addition, a plurality of processing units may be configured by one processor. A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by one or more of the various processors as a hardware structure.

In addition, specifically, the hardware structure of the various processors is an electric circuit (circuitry) obtained by combining circuit elements such as semiconductor elements.

The image acquisition unit 31 drives the X-ray source 3 to irradiate the subject H with X-rays, detects X-rays transmitted through the subject H using the first and second radiation detectors 5 and 6, and acquires the first and second radiographic images G1 and G2. At that time, imaging conditions, such as an imaging dose, a tube voltage, and an SID, are set. The imaging conditions may be set by an input operation of the operator through the input unit 9. The set imaging conditions are stored in the storage 23. In addition, the first and second radiographic images G1 and G2 may be acquired by a program different from the bone mineral information acquisition program and then stored in the storage 23. In this case, the image acquisition unit 31 is read from the storage 23 in order to process the first and second radiographic images G1 and G2 stored in the storage 23. In this embodiment, it is assumed that an image of the abdomen of the subject H is captured from the chest side and the first and second radiographic images G1 and G2 of the abdomen are acquired from the chest side.

The body thickness estimation unit 32 estimates the body thickness of the subject H for each pixel of the first and second radiographic images G1 and G2 on the basis of at least one of the first radiographic image G1 or the second radiographic image G2. Since the body thickness is estimated for each pixel of the first and second radiographic images G1 and G2, the body thickness estimation unit 32 estimates a body thickness distribution in at least one of the first radiographic image G1 or the second radiographic image G2. The body thickness estimation unit 32 estimates the body thickness using the first radiographic image G1 acquired by the radiation detector 5 close to the subject H. However, the second radiographic image G2 may be used. In addition, weighted subtraction may be performed between the corresponding pixels of the first radiographic image G1 and the second radiographic image G2 to generate a soft part image obtained by extracting only the soft part of the subject H included in each of the first and second radiographic images G1 and G2 and the body thickness of the subject H may be estimated using the soft part image. In addition, even in a case in which any of the images is used, a low-frequency image indicating a low-frequency component of the image may be generated and the body thickness may be estimated using the low-frequency image.

Figure 3:
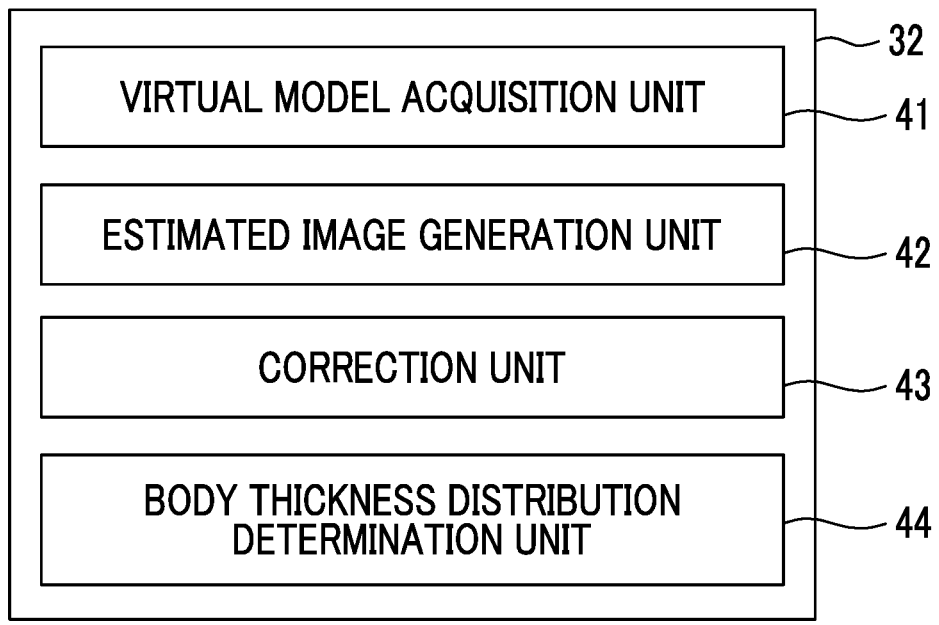
FIG. 3 is a block diagram schematically illustrating the configuration of a body thickness estimation unit.

In this embodiment, the body thickness estimation unit 32 estimates the body thickness of the subject H using, for example, the method disclosed in JP2015-043959A. FIG. 3 is a block diagram schematically illustrating the configuration of the body thickness estimation unit 32. As illustrated in FIG. 3, the body thickness estimation unit 32 comprises a virtual model acquisition unit 41, an estimated image generation unit 42, a correction unit 43, and a body thickness distribution determination unit 44.

The virtual model acquisition unit 41 acquires a virtual model K of the subject H having an initial body thickness distribution $TO(x, y)$. In this embodiment, the virtual model K of the subject H having the initial body thickness distribution $TO(x, y)$ is stored in the storage 23. The virtual model K is data virtually indicating the subject H in which the body thickness following the initial body thickness distribution $TO(x, y)$ is associated with each position on the xy plane.

The estimated image generation unit 42 generates a composite image of an estimated primary ray image obtained by estimating a primary ray image obtained by capturing an image of the virtual model K and an estimated scattered ray image obtained by estimating a scattered ray image obtained by capturing an image of the virtual model K as an estimated image obtained by estimating the first radiographic image G1 of the subject H, on the basis of the virtual model K.

The correction unit 43 corrects the initial body thickness distribution $TO(x, y)$ of the virtual model K on the basis of the estimated image and the first radiographic image G1 such that a difference between the estimated image and the first radiographic image G1 is reduced.

The estimated image generation unit 42 and the correction unit 43 repeat the generation of the estimated image and the correction of the body thickness distribution until the difference between the estimated image and the first radiographic image G1 satisfies predetermined end conditions.

The body thickness distribution determination unit 44 determines the body thickness distribution satisfying the end conditions to be the body thickness distribution of the first radiographic image G1, that is, the body thickness T(x, y) for each pixel.

Figure 4:
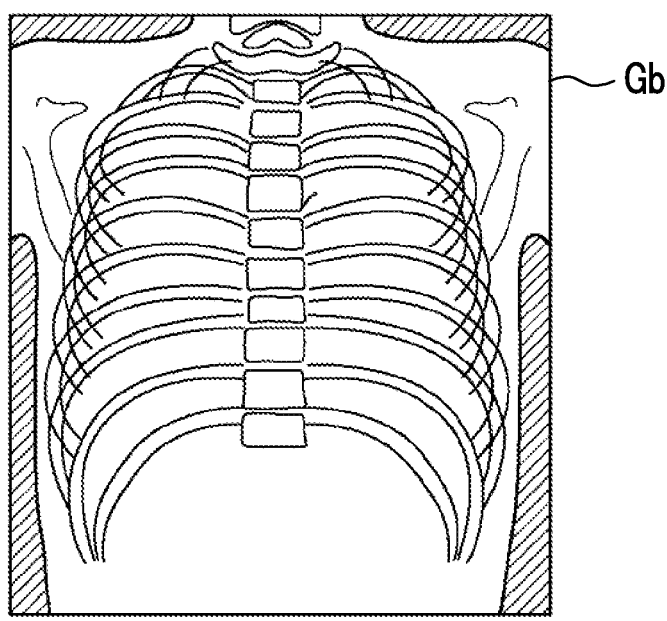
FIG. 4 is a diagram illustrating a bone part image.

The bone part pixel value acquisition unit 33 acquires the pixel value of the bone region of the subject H from the first and second radiographic images G1 and G2. Specifically, the bone part pixel value acquisition unit 33 performs weighted subtraction between the corresponding pixels of the first radiographic image G1 and the second radiographic image G2 to generate a bone part image Gb obtained by extracting only the bone part of the subject H included in each of the first and second radiographic images G1 and G2, as represented by, for example, the following Expression (1): Gb(x, y)=G1(x, y)−μ×G2(x, y) (1). In Expression (1), μ is a weighting coefficient. FIG. 4 is a diagram illustrating the bone part image Gb. In addition, the value of each pixel in the bone region of the bone part image Gb is a bone part pixel value.

In this embodiment, scattered ray components may be removed from the first radiographic image, the second radiographic image, the soft part image, and the bone part image by, for example, the method disclosed in JP2015-043959A. In addition, since the distances of the first radiographic image G1 and the second radiographic image G2 from the subject H are different from each other, the contents of scattered rays in the first radiographic image G1 and the second radiographic image G2 are different from each other. Therefore, a difference between the contents of scattered rays in the first radiographic image G1 and the second radiographic image G2 may be corrected.

The information acquisition unit 34 acquires bone mineral information indicating the bone mineral content of the bone region for each pixel of the bone region included in the first and second radiographic images G1 and G2. In this embodiment, the information acquisition unit 34 converts the pixel value of the bone region into a pixel value of a bone image acquired under reference imaging conditions to acquire the bone mineral information.

Figure 5:
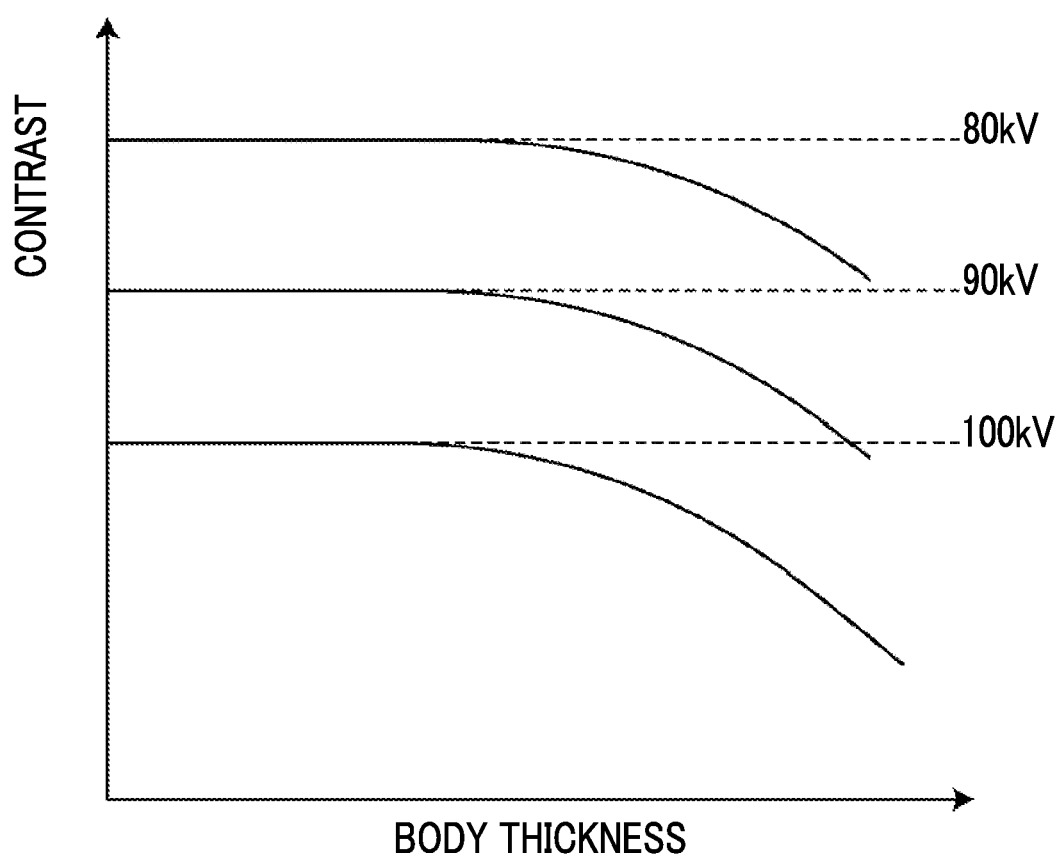
FIG. 5 is a diagram illustrating the relationship between the body thickness and the contrast of a bone part and a soft part.

Here, as the tube voltage applied to the X-ray source 3 becomes higher and the energy of X-rays becomes higher, the contrast of the soft part and the bone part in the radiographic image becomes lower. While X-rays are transmitted through the subject H, beam hardening in which low-energy components of the X-rays are absorbed by the subject H and the energy of the X-rays increases occurs. An increase in the energy of the X-rays due to the beam hardening becomes larger as the body thickness of the subject H becomes larger. FIG. 5 is a diagram illustrating the relationship between the body thickness and the contrast of the bone part and the soft part. In addition, FIG. 5 illustrates the relationship between the body thickness and the contrast of the bone part and the soft part at three tube voltages of 80 kV, 90 kV, and 100 kV. As illustrated in FIG. 5, as the tube voltage becomes higher, the contrast becomes lower. In addition, in a case in which the body thickness is greater than a certain value, as the body thickness becomes larger, the contrast becomes lower. Further, as the pixel value of the bone region in the bone part image Gb becomes larger, the contrast of the bone part and the soft part becomes higher. Therefore, the relationship illustrated in FIG. 5 shifts to a higher contrast side as the pixel value of the bone region in the bone part image Gb becomes larger.

Figure 6:
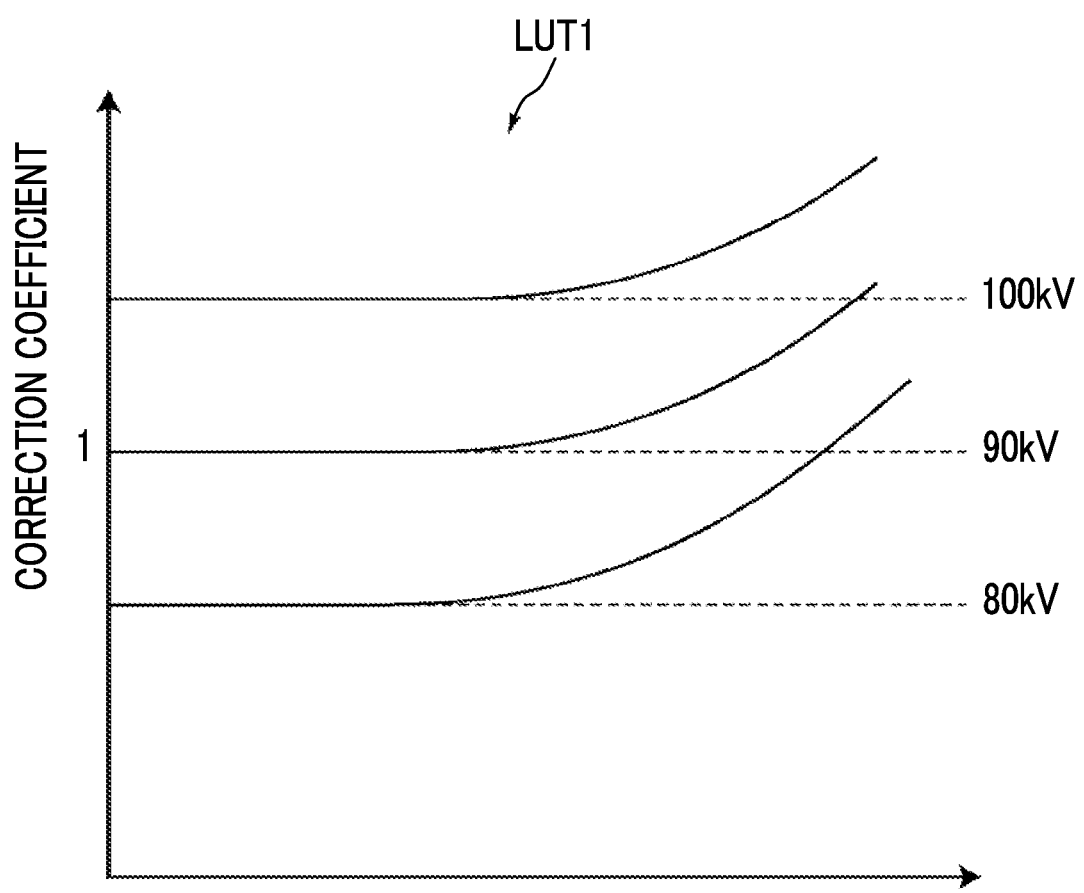
FIG. 6 is a diagram illustrating a look-up table for acquiring a correction coefficient.

In this embodiment, a look-up table in which the reference imaging condition is set to, for example, a tube voltage of 90 kV is prepared. The look-up table is used to acquire a correction coefficient for correcting a difference in contrast depending on a tube voltage at the time of imaging and a reduction in contrast caused by the influence of beam hardening. In addition, the look-up table is stored in the storage 23. FIG. 6 is a diagram illustrating the look-up table for acquiring the correction coefficient. As illustrated in FIG. 6, in a look-up table LUT1, as the tube voltage becomes higher and the body thickness becomes larger, the value of the correction coefficient becomes larger. In this embodiment, the reference imaging condition is a tube voltage of 90 kV. Therefore, in a case in which the tube voltage is 90 kV and the thickness is 0, the correction coefficient is 1. In FIG. 6, the look-up table LUT1 is two-dimensionally illustrated. However, the correction coefficient varies depending on the pixel value of the bone region. Therefore, in practice, the look-up table LUT1 is a three-dimensional table including an axis indicating the pixel value of the bone region.

The information acquisition unit 34 acquires a correction coefficient C0(x, y) for each pixel which corresponds to the imaging conditions and the body thickness distribution (x, y) with reference to the look-up table LUT1. Then, the information acquisition unit 34 multiplies each pixel (x, y) of the bone region in the bone part image Gb by the correction coefficient C0(x, y) to acquire bone mineral information B0(x, y) for each pixel of the bone region as represented by the following Expression (2): B0(x, y)=C0(x, y)×Gb(x, y) (2). The calculated bone mineral information B0(x, y) is acquired by capturing an image of the subject at a tube voltage of 90 kV which is the reference imaging condition and indicates the pixel value of the bone part in the bone region included in the radiographic image from which the influence of beam hardening has been removed.

In a case in which the image of the subject H is captured, a scattered ray removal grid for removing scattered rays incident on the first and second radiation detectors 5 and 6 may be used. Therefore, look-up tables corresponding to whether the scattered ray removal grid is present may be prepared and a look-up table for acquiring the correction coefficient may be selected according to whether the scattered ray removal grid is present. In addition, look-up tables corresponding to the types of scattered ray removal grids may be prepared and a look-up table corresponding to the type of scattered ray removal grid used at the time of imaging may be selected.

Figure 7:
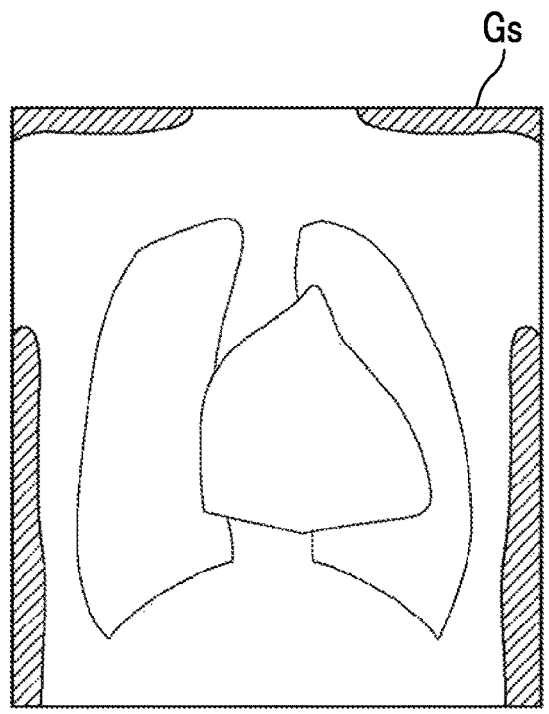
FIG. 7 is a diagram illustrating a soft part image.

The related information generation unit 35 generates information related to the bone mineral information. In this embodiment, the related information generation unit 35 performs weighted subtraction between the corresponding pixels of the first radiographic image G1 and the second radiographic image G2 to generate a soft part image Gs obtained by extracting only the soft part of the subject H included in each of the first and second radiographic images G1 and G2. FIG. 7 is a diagram illustrating the soft part image Gs. Then, the related information generation unit 35 generates a composite image Gc obtained by superimposing the bone mineral information B0(x, y) on the soft part image Gs as the related information.

In this embodiment, the bone mineral information may be superimposed on the bone part image Gb to generate the composite image Gc or the bone mineral information B0(x, y) may be superimposed on the first radiographic image G1 or the second radiographic image G2 to generate the composite image Gc.

Figure 8:
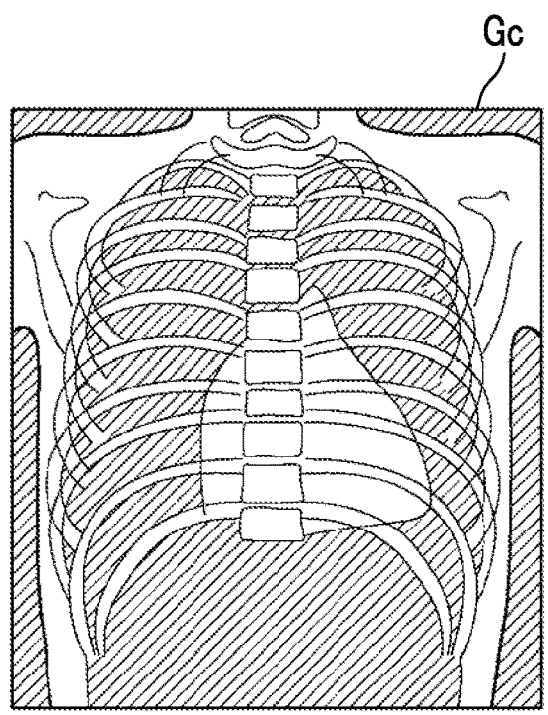
FIG. 8 is a diagram illustrating related information displayed on a display unit.

The display controller 36 displays the related information on the display unit 8. FIG. 8 is a diagram illustrating the related information displayed on the display unit 8. As illustrated in FIG. 8, the related information is the composite image Gc.

Figure 9:
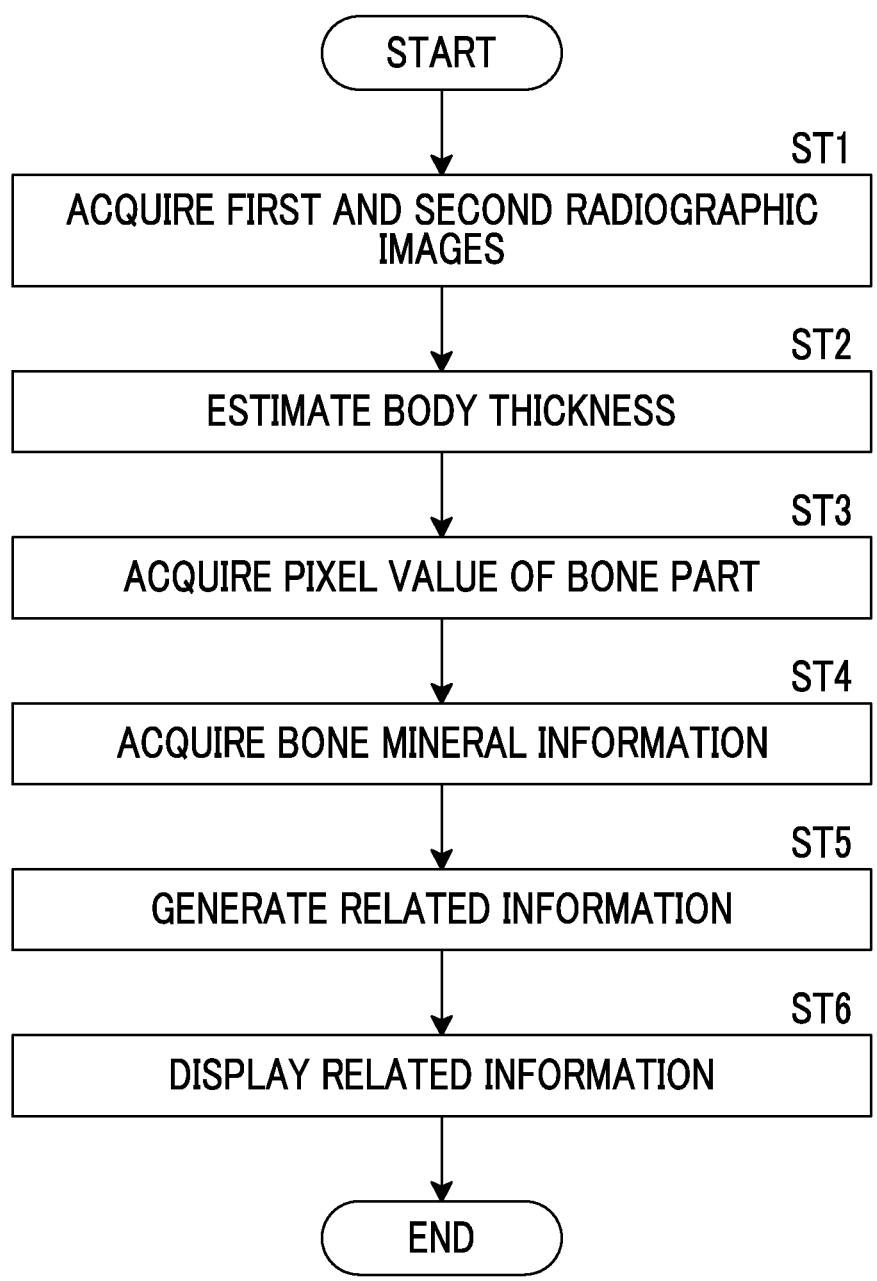
FIG. 9 is a flowchart illustrating a process performed in this embodiment.

Next, a process performed in this embodiment will be described. FIG. 9 is a flowchart illustrating the process performed in this embodiment. First, the image acquisition unit 31 directs the imaging apparatus 1 to capture images and acquires the first and second radiographic images G1 and G2 having different energy distributions (Step ST1). Then, the body thickness estimation unit 32 estimates the body thickness of the subject H for each pixel of at least one of the first radiographic image G1 or the second radiographic image G2 on the basis of the at least one of the first radiographic image G1 or the second radiographic image G2 (Step ST2). In addition, the bone part pixel value acquisition unit 33 acquires the pixel value of the bone region of the subject H from the first and second radiographic images G1 and G2 (Step ST3).

Then, the information acquisition unit 34 acquires bone mineral information indicating the bone mineral content of the bone region for each pixel of the bone region on the basis of the imaging conditions in a case in which the first and second radiographic images G1 and G2 have been acquired, the body thickness for each pixel, and the pixel value of the bone region (Step ST4). In addition, the related information generation unit 35 generates information related to the bone mineral information (Step ST5) and the display controller 36 displays the related information on the display unit 8 (Step ST6). Then, the process ends.

As such, according to this embodiment, the body thickness of the subject H is estimated for each pixel of at least one of the first radiographic image G1 or the second radiographic image G2 and the pixel value of the bone region of the subject H is acquired from the first and second radiographic images G1 and G2. Then, the bone mineral information indicating the bone mineral content of the bone region is acquired for each pixel of the bone region on the basis of the imaging conditions in a case in which the first and second radiographic images G1 and G2 have been acquired, the body thickness for each pixel, and the pixel value of the bone region. Therefore, it is possible to acquire the bone mineral information without using a dedicated apparatus unlike the DXA method. In addition, since the bone mineral information is acquired for each pixel of the bone region, it is possible to evaluate the bone mineral information for each part of the bone.

Figure 10:
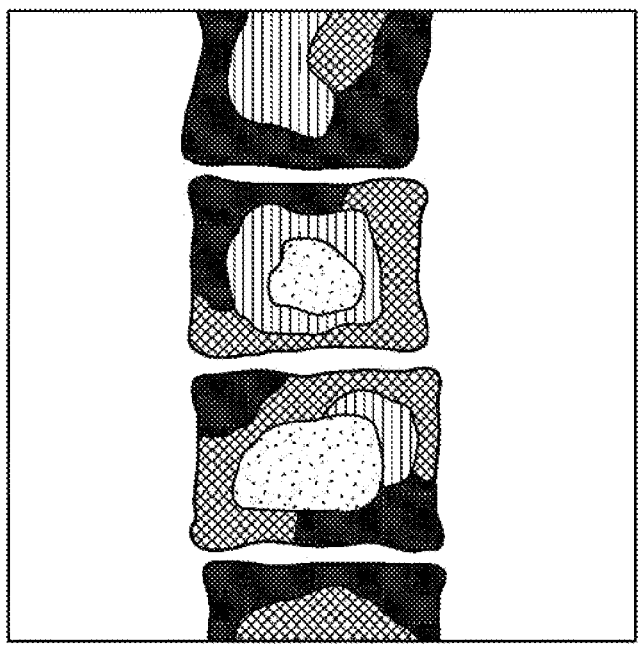
FIG. 10 is a diagram illustrating bone mineral information displayed on the display unit.
Figure 10:
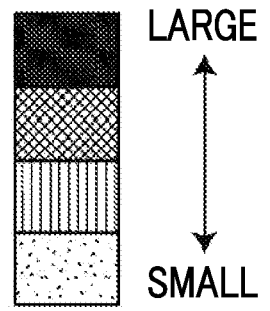

In the above-described embodiment, the composite image Gc obtained by superimposing the bone mineral information B0(x, y) on the soft part image Gs is generated as the related information. However, the invention is not limited thereto. The bone mineral information for each pixel acquired by the information acquisition unit 34 may be displayed as the related information. FIG. 10 is a diagram illustrating the bone mineral information displayed on the display unit 8. In addition, FIG. 10 illustrates only some vertebrae of the spine for simplicity of explanation. In this embodiment, since the bone mineral information is calculated for each pixel, the display of the bone mineral information makes it possible to check the distribution of the bone mineral content corresponding to the value of the bone mineral information. In particular, in a case in which different colors are mapped and displayed according to the value of the bone mineral information, it is possible to more easily check the distribution of the bone mineral content. Further, in FIG. 10, the distribution of the bone mineral content is indicated by a difference in hatching.

In addition, the related information generation unit 35 may calculate bone strength from the bone mineral information and may use the calculated bone strength as the related information. In this case, the bone strength can be calculated on the basis of the bone mineral information and an index value indicating bone texture. In addition, the density of a trabecular structure forming the bone is used as the index value indicating the texture. Therefore, the related information generation unit 35 extracts a high-frequency component of the image of the bone region in the bone part image Gb. Any method, such as Fourier transform, wavelet transform, or a method using a high-pass filter, can be used as a method for extracting the high-frequency component. Then, the related information generation unit 35 calculates a variance value of the high-frequency components for each pixel of the bone region. Here, as the density of the trabecular structure becomes lower, the calculated variance value of the high-frequency components becomes smaller. Therefore, the related information generation unit 35 calculates bone strength using the operation of the bone mineral information x the variance value. Here, since the bone mineral information and the variance value are acquired for each pixel of the bone region, the bone strength is also calculated for each pixel.

In addition, texture features by a simultaneous occurrence matrix, such as uniformity, contrast, correlation, or entropy, may be used as the index value indicating the texture. The simultaneous occurrence matrix is a matrix indicating the distribution of signal values of pixels in an image and represents the frequency of the signal value of a pixel adjacent to the pixel having a certain signal value as a matrix.

Figure 11:
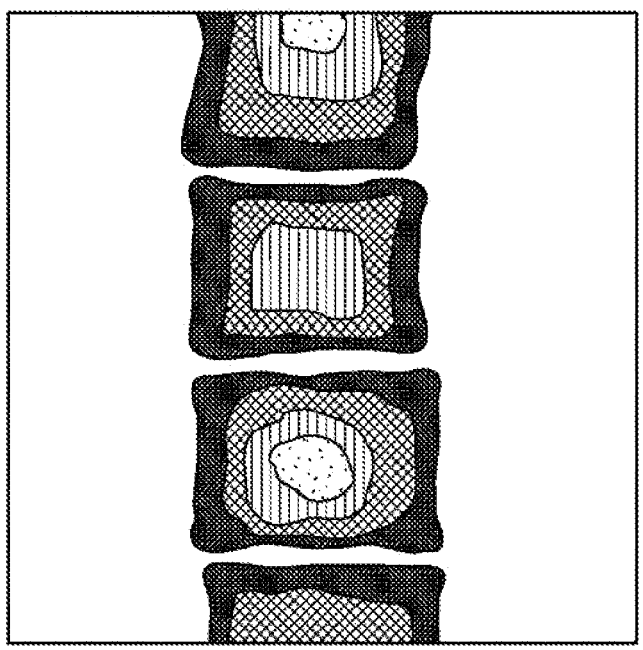
FIG. 11 is a diagram illustrating bone strength displayed on the display unit.
Figure 11:
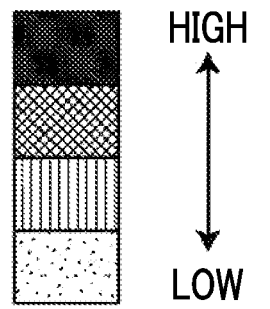

FIG. 11 is a diagram illustrating the bone strength displayed on the display unit 8. FIG. 11 illustrates only some vertebrae of the spine for simplicity of explanation. In this embodiment, since the bone strength is calculated for each pixel, the display of the bone strength makes it possible to check the distribution of the bone strength. In particular, in a case in which different colors are mapped and displayed according to the bone strength, it is possible to more easily check the distribution of the bone strength. Further, in FIG. 11, the distribution of the bone strength is indicated by a difference in hatching.

In a case in which the bone strength is displayed, the bone strength may be displayed so as to be superimposed on the soft part image Gs or may be displayed so as to be superimposed on the bone part image Gb. In addition, the bone strength may be displayed so as to be superimposed on the first radiographic image G1 or the second radiographic image G2.

Figure 12:
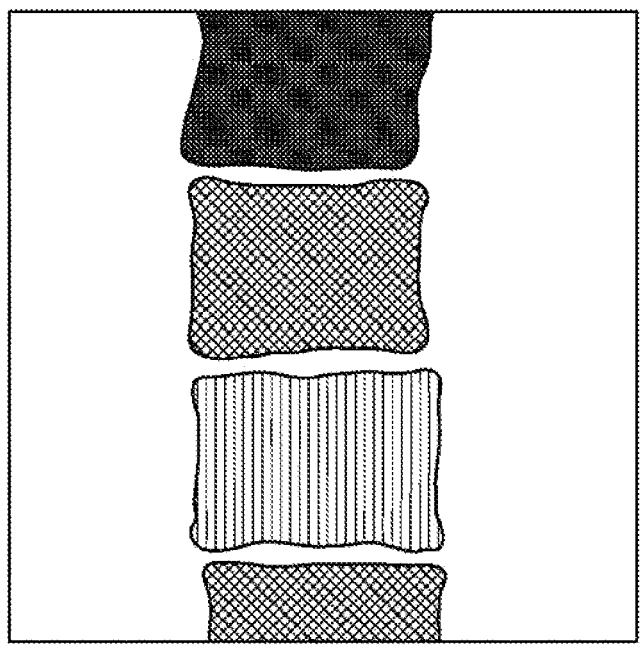
FIG. 12 is a diagram illustrating statistical values of the bone mineral information displayed on the display unit.
Figure 12:
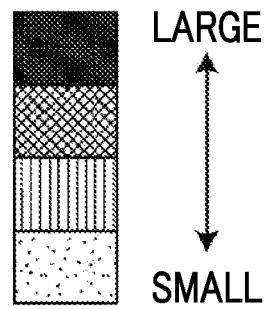

In a case in which a plurality of bones are included in the first and second radiographic images G1 and G2, the related information generation unit 35 may generate the related information for each bone. In this case, a statistical value of bone mineral information for each bone may be used as the related information. In addition, for example, the mean, median, maximum value, and minimum value of the bone mineral information for each bone can be used as the statistical values. FIG. 12 is a diagram illustrating the statistical value of the bone mineral information displayed on the display unit 8. In addition, FIG. 12 illustrates only some vertebrae of the spine for simplicity of explanation. In this embodiment, since the statistical value of the bone mineral information is calculated for each bone, it is possible to check the bone mineral information for each bone. In particular, in a case in which different colors are mapped and displayed according to the bone mineral information, it is possible to more easily check the bone mineral information for each bone. Further, in FIG. 12, a difference between the statistical values of the bone mineral information is indicated by a difference in hatching.

Figure 13:
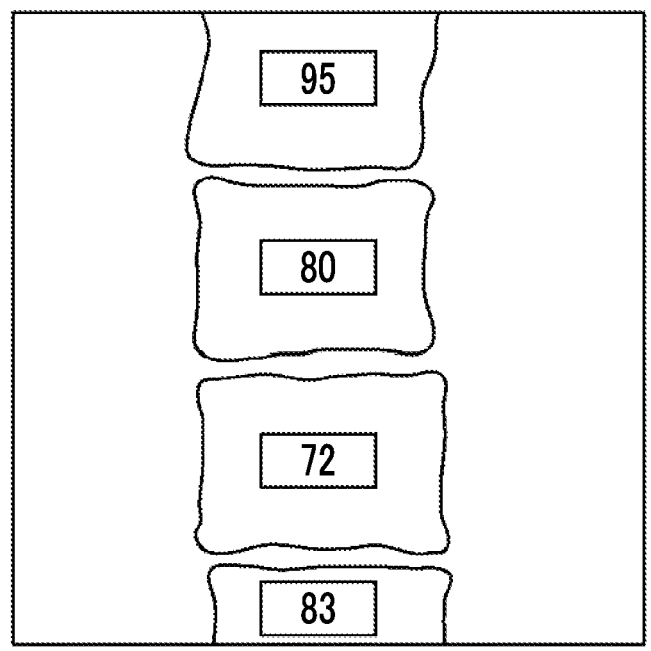
FIG. 13 is a diagram illustrating the statistical values of the bone mineral information displayed on the display unit.

In FIG. 12, the statistical values of the bone mineral information are mapped by different colors corresponding to the magnitudes of the statistical values. However, as illustrated in FIG. 13, the statistical value of the bone mineral information may be displayed as a numerical value.

Figure 14:
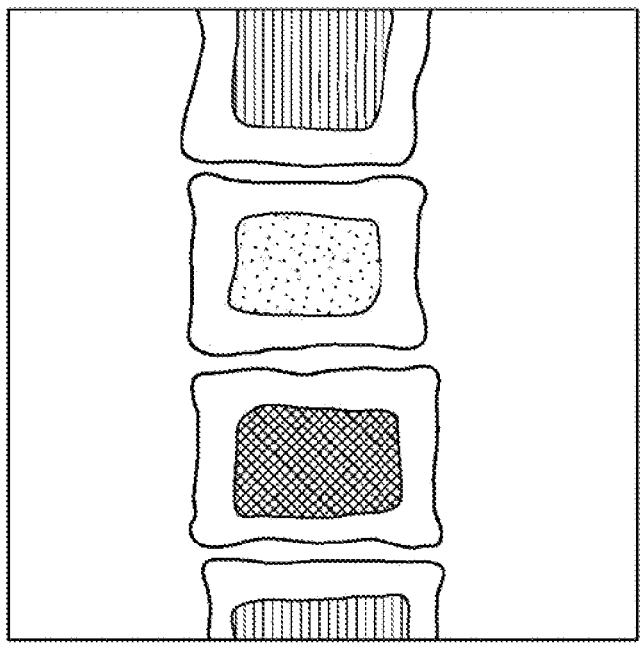
FIG. 14 is a diagram illustrating the statistical values of the bone mineral information of partial regions in the bone region displayed on the display unit.
Figure 14:
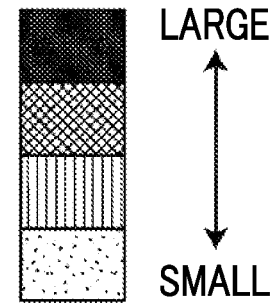

In addition, the related information generation unit 35 may generate the related information of a partial region in the bone region for one bone. In this case, the statistical value of the bone mineral information of the partial region can be used as the related information. Further, for example, the mean, median, maximum value, and minimum value of the bone mineral information of the partial region can be used as the statistical values. FIG. 14 is a diagram illustrating the statistical value of the bone mineral information of the partial region displayed on the display unit 8. In FIG. 14, for simplicity of explanation, a cancellous bone region is a partial region of the vertebra and the statistical value of the bone mineral information of the cancellous bone region is displayed. In this embodiment, since the statistical value of the bone mineral information is calculated for each bone, it is possible to check the bone mineral information of each bone. In particular, in a case in which different colors are mapped and displayed according to the value of the bone mineral information, it is possible to more easily check the bone mineral information of each bone. Further, in FIG. 14, the difference between the statistical values of the bone mineral information is indicated by a difference in hatching.

As such, since the related information for the cancellous bone region in the bone region is generated, for example, the degree of activation of osteoblasts in the cancellous bone can be checked by medication for osteoporosis. Therefore, it is possible to easily check the effect of medicine treatment.

In FIG. 14, the related information only for the cancellous bone region is generated. However, as illustrated in FIG. 15, the statistical value of the bone mineral information of a cortical bone region in addition to the cancellous bone region may be generated and displayed as the related information.

Figure 15:
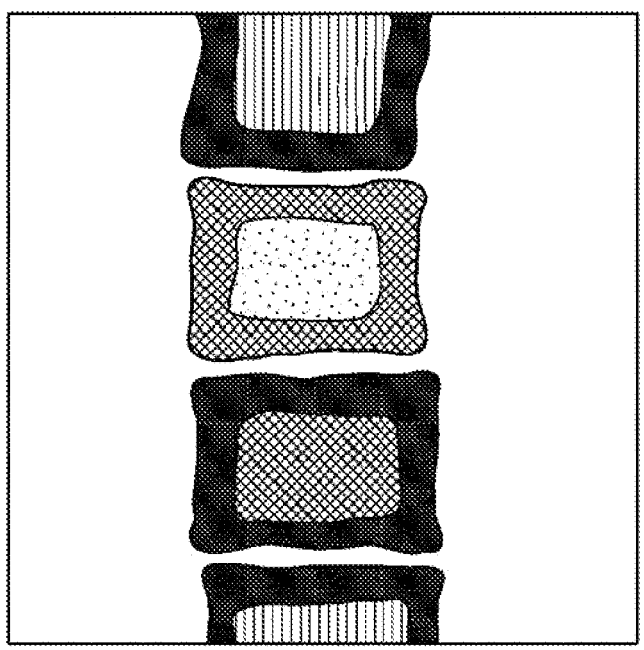
FIG. 15 is a diagram illustrating the statistical values of the bone mineral information of the partial regions displayed on the display unit.
Figure 15:
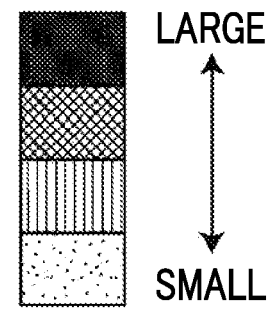
Figure 16:
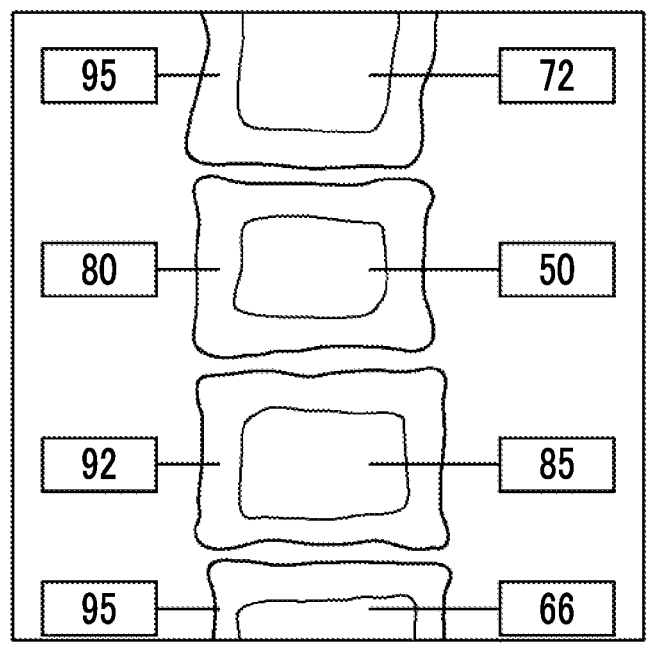
FIG. 16 is a diagram illustrating the statistical values of the bone mineral information of the partial regions displayed on the display unit.

In FIGS. 14 and 15, the statistical values of the bone mineral information calculated for each partial region are mapped by different colors corresponding to the magnitudes of the statistical values. However, as illustrated in FIG. 16, the statistical value of the bone mineral information may be displayed as a numerical value. In addition, in FIG. 16, the numerical values of the statistical values for both the cancellous bone region and the cortical bone region are displayed. However, the numerical value of the statistical value only for the cancellous bone region or only for the cortical bone region may be displayed.

Figure 17:
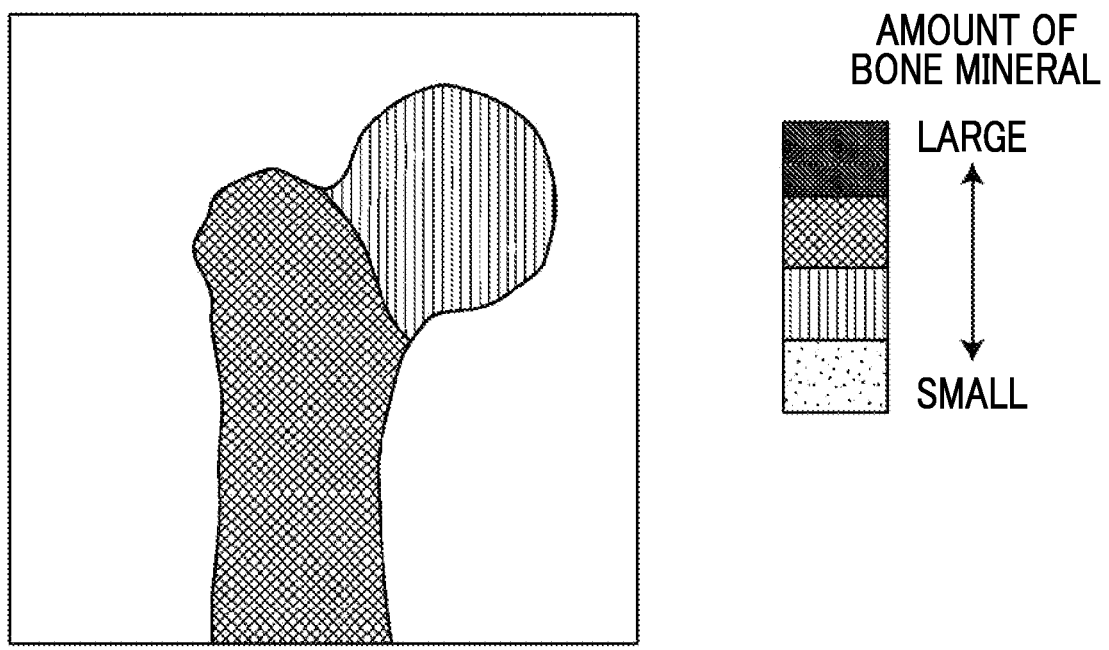
FIG. 17 is a diagram illustrating the statistical values of the bone mineral information of the partial regions displayed on the display unit.

In the above-described embodiment, the bone region is divided into the cortical bone region and the cancellous bone region. However, the invention is not limited thereto. For example, as illustrated in FIG. 17, the femur may be divided into a femoral neck region and the other region, the statistical values of bone mineral information for the regions may be generated as the related information and then displayed. In this case, similarly to FIG. 16, the statistical value of the bone mineral information may be displayed as a numerical value.

Figure 18:
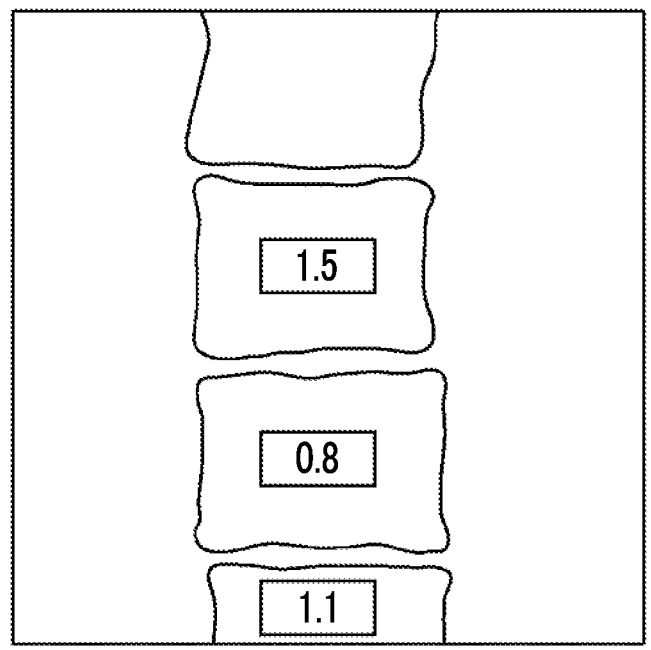
FIG. 18 is a diagram illustrating the comparison result between the statistical values of the bones displayed on the display unit.

In a case in which a plurality of bones are included in the first and second radiographic images, the related information generation unit 35 may generate the comparison result between the bone mineral information items of the bones as the related information. In this case, the related information generation unit 35 calculates the statistical value of bone mineral information for each bone and generates, as the related information, a difference value or ratio between the statistical values of the bone mineral information items of a certain bone as a reference bone and other bones. FIG. 18 is a diagram illustrating the comparison result between the statistical values for the bones displayed on the display unit 8. FIG. 18 illustrates only some vertebrae of the spine for simplicity of explanation. The numerical values of the ratios between the statistical values of the bone mineral information items of the uppermost vertebra as a reference vertebra and other vertebrae among the displayed vertebrae are illustrated as the comparison result. As such, since the comparison result between the bone mineral information items of the bones is generated as the related information and is then displayed, it is possible to check the bone mineral content of other bones with respect to a certain bone as the reference bone.

Figure 19:
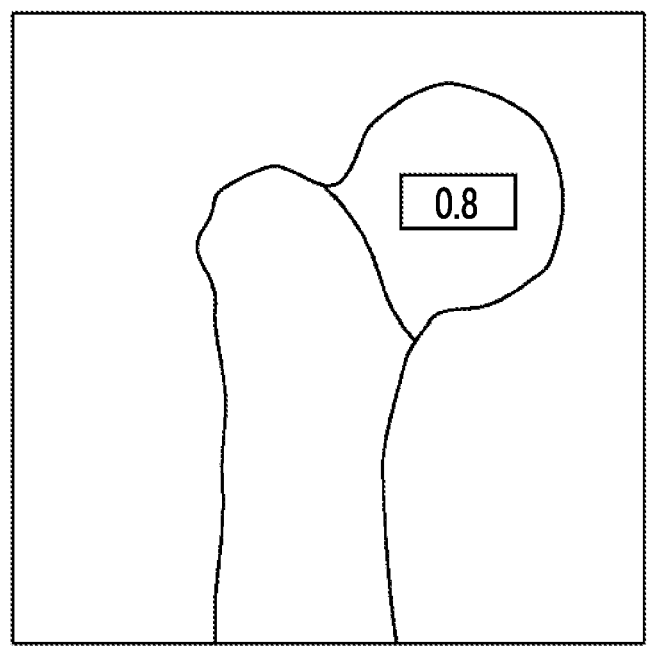
FIG. 19 is a diagram illustrating the comparison result between the statistical values of the partial regions displayed on the display unit.

The related information generation unit 35 may generate, as the related information, the comparison result between the bone mineral information items of partial regions in the bone region for one bone. In this case, the related information generation unit 35 calculates the statistical value of the bone mineral information of each partial region in the bone region and generates, as the related information, a difference value or ratio between the statistical values of the bone mineral information items of a certain partial region as a reference partial region and other partial regions. FIG. 19 is a diagram illustrating the comparison result between the statistical values of the partial regions displayed on the display unit 8. FIG. 19 illustrates only a portion of the femur for simplicity of explanation. In addition, the numerical value of the ratio between the statistical values of the bone mineral information items of a femoral neck region and other regions in the displayed femur is illustrated as the comparison result. As such, since the comparison result between the bone mineral information items of the partial regions in the bone region is generated as the related information and is then displayed, it is possible to check the bone mineral content of other parts with respect to a certain part in one bone.

In addition, the related information generation unit 35 may generate, as the related information, the comparison result between bone mineral information items acquired for the same subject at different acquisition dates and times. In this case, the related information generation unit 35 calculates the statistical values of the latest bone mineral information and the past bone mineral information for the same subject. The statistical values may be calculated for each bone or the statistical values of all of the bones included in the radiographic image may be calculated. Then, the related information generation unit 35 generates the comparison result between the past statistical value and the latest statistical value as the related information. The ratio or difference value between the past statistical value and the latest statistical value can be used as the comparison result.

Figure 20:
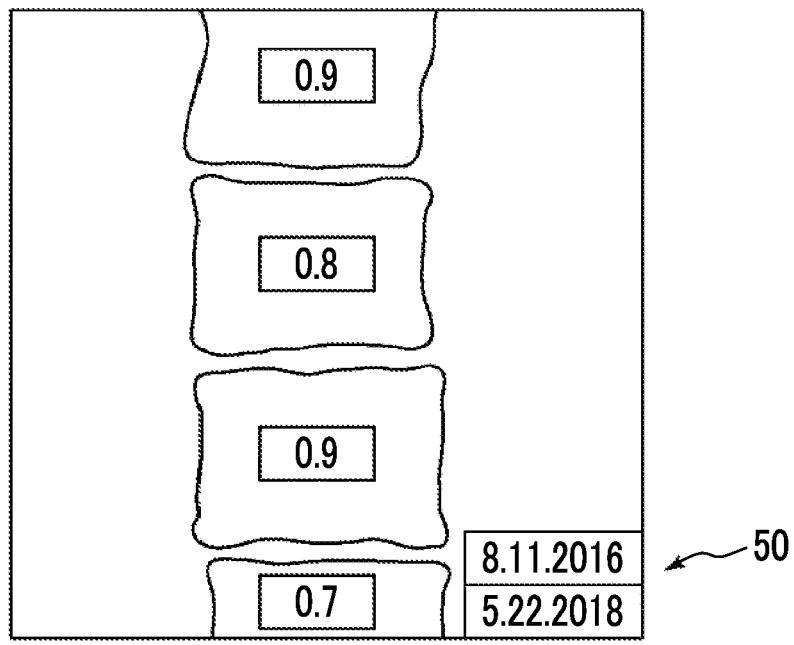
FIG. 20 is a diagram illustrating the comparison result between bone mineral information items displayed on the display unit.

FIG. 20 is a diagram illustrating the comparison result between the bone mineral information items displayed on the display unit 8. In addition, FIG. 20 illustrates, as the comparison result, the ratio between the statistical values of the past bone mineral information and the latest bone mineral information of each vertebra. Further, FIG. 20 illustrates the date and time when the past bone mineral information was acquired and the date and time 50 when the latest bone mineral information was acquired. As such, since the comparison result between the bone mineral information items acquired from the radiographic images acquired at different dates and times for the same subject is generated as the related information and is then displayed, it is possible to recognize the degree of progress of the disease or the degree of medicine treatment for the subject H. In addition, it is easy to decide a treatment plan on the basis of the degree of progress of the disease or the degree of medicine treatment.

Figure 21:
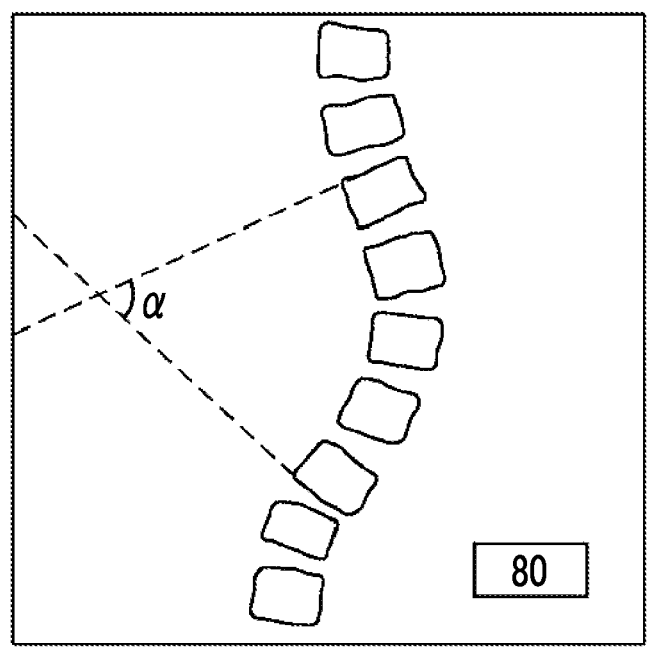
FIG. 21 is a diagram illustrating a bone fracture risk displayed on the display unit.

In a case in which the bone region is the vertebra, the related information generation unit 35 may generate, as the related information, information indicating a bone fracture risk generated from spinal alignment and the bone mineral information. For example, as illustrated in FIG. 21, in a case of a subject suffering from lateral curvature, the related information generation unit 35 calculates a Cobb angle α as the spinal alignment and calculates the bone fracture risk on the basis of the Cobb angle α and the bone mineral information. Here, the Cobb angle is the angle formed between two straight lines that extend from the outer edges of the vertebrae inclined at the maximum angle above and below the vertebra (apical vertebra) which is the apex of the curvature and intersect each other. In addition, the relationship between the bone fracture risk, and the Cobb angle α and the bone mineral information is determined by a table or a computation expression. The related information generation unit 35 calculates the bone fracture risk from the Cobb angle and the bone mineral information with reference to the table or the computation expression. In FIG. 21, the calculated bone fracture risk is illustrated as a numerical value (here, 80). In addition, the bone fracture risk becomes higher as the numerical value becomes larger. As such, since the bone fracture risk is generated as the related information and is then displayed, it is possible to guide a patient who is at high risk of bone fracture such that bone fracture is prevented.

In the above-described embodiment, the first and second radiographic images G1 and G2 are acquired by the one-shot method. However, the first and second radiographic images G1 and G2 may be acquired by a so-call two-shot method that performs imaging two times. In this case, any of the imaging conditions in a case in which the first radiographic image G1 has been acquired and the imaging conditions in a case in which the second radiographic image G2 has been acquired may be used as the imaging conditions. In addition, in the case of the two-shot method, the position of the subject H included in the first radiographic image G1 and the second radiographic image G2 is likely to be shifted by the movement of the subject H. Therefore, it is preferable to perform the process according to this embodiment after the position of the subject is aligned in the first radiographic image G1 and the second radiographic image G2. For example, the method disclosed in JP2011-255060A can be used as the position alignment process. The method disclosed in JP2011-255060A generates a plurality of first band images and a plurality of second band images indicating structures having different frequency bands for each of the first and second radiographic images G1 and G2, acquires the amount of deviation between the corresponding positions in the first and second band images with the corresponding frequency band, and aligns the positions of the first radiographic image G1 and the second radiographic image G2 on the basis of the amount of deviation.

In the above-described embodiment, the display of various kinds of related information has been described. However, a plurality of different related information items may be displayed on the display unit 8 at the same time.

In the above-described embodiment, image processing is performed using the radiographic images acquired by the system that captures the radiographic images of the subject using the first and second radiation detectors 5 and 6. However, the present disclosure may also be applied to a case in which the first and second radiographic images G1 and G2 are acquired using a stimulable phosphor sheet as the detector. In this case, the first and second radiographic images G1 and G2 may be acquired as follows: two stimulable phosphor sheets overlap each other and are irradiated with X-rays transmitted through the subject H; the radiographic image information of the subject H is accumulated and recorded on each of the stimulable phosphor sheets; and the radiographic image information is photoelectrically read from each of the stimulable phosphor sheets.

What is claimed is:

1. A bone mineral information acquisition apparatus comprising a processor that is configured to:
   estimate a body thickness of a subject including a bone part and a soft part for each pixel of at least one of a first radiographic image or a second radiographic image which includes a primary ray component and a scattered ray component, on the basis of the at least one of the first radiographic image or the second radiographic image, the first and second radiographic images being acquired by radiations that have different energy distributions and have been transmitted through the subject;
   acquire a pixel value of a bone region of the subject from the first and second radiographic images; and
   acquire bone mineral information indicating a bone mineral content of the bone region for each pixel of the bone region on the basis of imaging conditions in a case in which the at least one image has been acquired, the body thickness for each pixel, and the pixel value of the bone region,
   wherein the processor is configured to acquire the bone mineral information by converting each pixel value of the bone region into a pixel value of the bone region acquired on the basis of a reference imaging condition, and by converting the pixel value of the bone region on the basis of a correction coefficient corresponding to at least one of information on the reference imaging condition, information on beam hardening corresponding to the body thickness, or information on whether a scattered ray removal grid is present during imaging.

2. The bone mineral information acquisition apparatus according to claim 1,
   wherein the first and second radiographic images are acquired by irradiating two detectors that overlap each other with the radiation transmitted through the subject.

3. The bone mineral information acquisition apparatus according to claim 1,
   wherein the first and second radiographic images are acquired by alternately irradiating one detector with the radiations that have different energy distributions and have been transmitted through the subject.

4. The bone mineral information acquisition apparatus according to claim 1,
   wherein the reference imaging condition is a tube voltage that is applied to a radiation source in a case in which the first and second radiographic images are acquired.

5. The bone mineral information acquisition apparatus according to claim 1, wherein the processor is configured to:
   cause display of information related to the bone mineral information on a display.

6. The bone mineral information acquisition apparatus according to claim 5,
wherein the processor is configured to cause display, as the related information, a soft part image indicating a soft region of the subject, a bone part image indicating the bone region of the subject, and a composite image obtained by superimposing the bone mineral information on the first radiographic image or the second radiographic image on the display, the soft part image and the bone part image being acquired from the first and second radiographic images.

7. A bone mineral information acquisition method comprising:
estimating a body thickness of a subject including a bone part and a soft part for each pixel of at least one of a first radiographic image or a second radiographic image which includes a primary ray component and a scattered ray component, on the basis of the at least one of the first radiographic image or the second radiographic image, the first and second radiographic images being acquired by radiations that have different energy distributions and have been transmitted through the subject;
acquiring a pixel value of a bone region of the subject from the first and second radiographic images; and
acquiring bone mineral information indicating a bone mineral content of the bone region for each pixel of the bone region on the basis of imaging conditions in a case in which the at least one image has been acquired, the body thickness for each pixel, and the pixel value of the bone region,
wherein acquiring the bone mineral information includes converting each pixel value of the bone region into a pixel value of the bone region acquired on the basis of a reference imaging condition, and converting the pixel value of the bone region on the basis of a correction coefficient corresponding to at least one of information indicating the reference imaging condition, information indicating beam hardening corresponding to the body thickness, or information indicating whether a scattered ray removal grid is present during imaging.

8. A non-transitory computer-readable storage medium that stores a bone mineral information acquisition program that causes a computer to perform:
estimating a body thickness of a subject including a bone part and a soft part for each pixel of at least one of a first radiographic image or a second radiographic image which includes a primary ray component and a scattered ray component, on the basis of the at least one of the first radiographic image or the second radiographic image, the first and second radiographic images being acquired by radiations that have different energy distributions and have been transmitted through the subject;
acquiring a pixel value of a bone region of the subject from the first and second radiographic images; and
acquiring bone mineral information indicating a bone mineral content of the bone region for each pixel of the bone region on the basis of imaging conditions in a case in which the at least one image has been acquired, the body thickness for each pixel, and the pixel value of the bone region,
wherein acquiring the bone mineral information includes converting each pixel value of the bone region into a pixel value of the bone region acquired on the basis of a reference imaging condition, and converting the pixel value of the bone region on the basis of a correction coefficient corresponding to at least one of information indicating the reference imaging condition, information indicating beam hardening corresponding to the body thickness, or information indicating whether a scattered ray removal grid is present during imaging.

9. A bone mineral information acquisition apparatus comprising a processor that is configured to:
estimate a body thickness of a subject including a bone part and a soft part for each pixel of at least one of a first radiographic image or a second radiographic image which includes a primary ray component and a scattered ray component, on the basis of the at least one of the first radiographic image or the second radiographic image, the first and second radiographic images being acquired by radiations that have different energy distributions and have been transmitted through the subject;
acquire a pixel value of a bone region of the subject from the first and second radiographic images;
acquire bone mineral information indicating a bone mineral content of the bone region for each pixel of the bone region on the basis of imaging conditions in a case in which the at least one image has been acquired, the body thickness for each pixel, and the pixel value of the bone region; and
cause display of information related to the bone mineral information on a display, the related information including a soft part image indicating a soft region of the subject, a bone part image indicating the bone region of the subject, and a composite image obtained by superimposing the bone mineral information on the first radiographic image or the second radiographic image on the display, the soft part image and the bone part image being acquired from the first and second radiographic images.

10. The bone mineral information acquisition apparatus according to claim 9,
wherein the processor is configured to cause display of bone strength calculated from the bone mineral information as the related information on the display.

11. The bone mineral information acquisition apparatus according to claim 9,
wherein, in a case in which the subject includes a plurality of bones, the processor is configured to cause display of the related information acquired for each bone on the display.

12. The bone mineral information acquisition apparatus according to claim 9,
wherein the processor is configured to cause display of the related information on a partial region in the bone region on the display.

13. The bone mineral information acquisition apparatus according to claim 12,
wherein the partial region is a cancellous bone region in the bone region.

14. The bone mineral information acquisition apparatus according to claim 9,
wherein, in a case in which the subject includes a plurality of bones, the processor is configured to cause display of a comparison result between the bone mineral information items of the bones as the related information on the display.

15. The bone mineral information acquisition apparatus according to claim 9,
wherein the processor is configured to cause display of a comparison result between the bone mineral information items of the partial regions in the bone region as the related information on the display.

16. The bone mineral information acquisition apparatus according to claim 9,
wherein the processor is configured to cause display of a comparison result between the bone mineral information and past bone mineral information acquired at different dates and times for the same subject as the related information on the display.

17. The bone mineral information acquisition apparatus according to claim 9,
wherein, in a case in which the bone region is a vertebra region, the related information indicates a bone fracture risk which is generated from spinal alignment and the bone mineral information on the display.

18. The bone mineral information acquisition apparatus according to claim 9,
wherein the processor is configured to generate the related information.

19. A bone mineral information acquisition method comprising:
estimating a body thickness of a subject including a bone part and a soft part for each pixel of at least one of a first radiographic image or a second radiographic image which includes a primary ray component and a scattered ray component, on the basis of the at least one of the first radiographic image or the second radiographic image, the first and second radiographic images being acquired by radiations that have different energy distributions and have been transmitted through the subject;
acquiring a pixel value of a bone region of the subject from the first and second radiographic images;
acquiring bone mineral information indicating a bone mineral content of the bone region for each pixel of the bone region on the basis of imaging conditions in a case in which the at least one image has been acquired, the body thickness for each pixel, and the pixel value of the bone region; and
displaying information related to the bone mineral information on a display, the displayed information including a soft part image indicating a soft region of the subject, a bone part image indicating the bone region of the subject, and a composite image obtained by superimposing the bone mineral information on the first radiographic image or the second radiographic image on the display, the soft part image and the bone part image being acquired from the first and second radiographic images.

20. A non-transitory computer-readable storage medium that stores a bone mineral information acquisition program that causes a computer to perform:
estimating a body thickness of a subject including a bone part and a soft part for each pixel of at least one of a first radiographic image or a second radiographic image which includes a primary ray component and a scattered ray component, on the basis of the at least one of the first radiographic image or the second radiographic image, the first and second radiographic images being acquired by radiations that have different energy distributions and have been transmitted through the subject;
acquiring a pixel value of a bone region of the subject from the first and second radiographic images;
acquiring bone mineral information indicating a bone mineral content of the bone region for each pixel of the bone region on the basis of imaging conditions in a case in which the at least one image has been acquired, the body thickness for each pixel, and the pixel value of the bone region; and
displaying information related to the bone mineral information on a display, the displayed information including a soft part image indicating a soft region of the subject, a bone part image indicating the bone region of the subject, and a composite image obtained by superimposing the bone mineral information on the first radiographic image or the second radiographic image on the display, the soft part image and the bone part image being acquired from the first and second radiographic images.

* * * * *